United States Patent
Dunaway (10) Patent No.: US 10,949,558 B2
(45) Date of Patent: *Mar. 16, 2021

(54) SECURE ACCESS TO HEALTHCARE INFORMATION

(71) Applicant: INTERNATIONAL BUSINESS MACHINES CORPORATION, Armonk, NY (US)

(72) Inventor: Fredrick T. Dunaway, Constable, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/782,149

(22) Filed: Oct. 12, 2017

(65) Prior Publication Data

US 2018/0046822 A1 Feb. 15, 2018

Related U.S. Application Data

(63) Continuation of application No. 14/674,305, filed on Mar. 31, 2015, now Pat. No. 9,953,181, which is a
(Continued)

(51) Int. Cl.
*G06F 21/00* (2013.01)
*G06F 21/62* (2013.01)
(Continued)

(52) U.S. Cl.
CPC .......... *G06F 21/6218* (2013.01); *G06F 19/00* (2013.01); *G06F 21/00* (2013.01);
(Continued)

(58) Field of Classification Search
CPC .... G06F 21/6218; G06F 21/602; G06F 21/00; G06F 21/6245; G06F 21/604; G06F 2221/2141; G16H 10/60
See application file for complete search history.

(56) References Cited

U.S. PATENT DOCUMENTS

5,555,192 A * 9/1996 Grube .................. H04W 12/12
340/7.25
7,466,232 B2 12/2008 Neuwirth
(Continued)

*Primary Examiner* — Shewaye Gelagay
*Assistant Examiner* — Carlton Johnson
(74) *Attorney, Agent, or Firm* — Brian Restauro; Andrew M. Calderon; Roberts Calderon Safran & Cole, P.C.

(57) ABSTRACT

A system and method for providing or exchanging healthcare information (e.g., medical information) to authorized users in a secure manner. The method is implemented in a computer infrastructure having computer executable code tangibly embodied on a computer readable storage medium having programming instructions operable to: assign identification information to a plurality of users and a plurality of items; associate the identification information of a user of the plurality of users with one or more items of the plurality of items; set-up security policies including predetermined locations, within predetermined stages within a sequence and during predetermined times; and provide the user access to the one or more items when there is a matching between the identification information of the user and the one or more items, and all of the security policies associated with the user and the one or more of the plurality of items are met.

20 Claims, 5 Drawing Sheets

Related U.S. Application Data continuation of application No. 12/943,964, filed on Nov. 11, 2010, now Pat. No. 9,032,512.

(51) Int. Cl.
*G06F 21/60* (2013.01)
*G16H 10/60* (2018.01)
*G06F 19/00* (2018.01)

(52) U.S. Cl.
CPC .......... *G06F 21/602* (2013.01); *G06F 21/604* (2013.01); *G06F 21/6245* (2013.01); *G16H 10/60* (2018.01); *G06F 2221/2141* (2013.01)

(56) References Cited

U.S. PATENT DOCUMENTS

| | | | |
|---|---|---|---|
| 7,706,896 B2 | 4/2010 | Music et al. | |
| 2003/0227386 A1* | 12/2003 | Pulkkinen | A61B 5/1113 340/573.1 |
| 2005/0062603 A1* | 3/2005 | Fuerst | G06K 19/07758 340/539.12 |
| 2005/0125694 A1 | 6/2005 | Fakes et al. | |
| 2005/0182661 A1 | 8/2005 | Allard et al. | |
| 2005/0231467 A1 | 10/2005 | Gold | |
| 2007/0078686 A1 | 4/2007 | Dettinger et al. | |
| 2007/0136103 A1 | 6/2007 | Kim et al. | |
| 2007/0180259 A1 | 8/2007 | Bulot et al. | |
| 2008/0100443 A1* | 5/2008 | Grunwald | H04L 63/0492 340/572.1 |
| 2008/0303638 A1 | 12/2008 | Nguyen et al. | |
| 2008/0316045 A1 | 12/2008 | Sriharto et al. | |
| 2009/0085741 A1 | 4/2009 | Ravi et al. | |
| 2009/0216587 A1* | 8/2009 | Dwivedi | G06F 21/31 705/7.12 |
| 2009/0228525 A1 | 9/2009 | Fridrich | |
| 2010/0090004 A1 | 4/2010 | Sands et al. | |
| 2010/0305971 A1 | 12/2010 | McLaren et al. | |
| 2012/0066502 A1 | 3/2012 | Borneman et al. | |

* cited by examiner

SECURE ACCESS TO HEALTHCARE INFORMATION

TECHNICAL FIELD

The present invention generally relates to managing of healthcare information in a secure manner and more particularly, to a system and method for providing or exchanging healthcare information (e.g., medical information) to authorized users.

BACKGROUND

Many government and regulatory agencies require that medical records remain private and secure. These regulations include, for example, The Health Insurance Portability and Accountability Act of 1996 (HIPAA) Privacy and Security Rule. In addition to such rules, it is very important from a patient standpoint to maintain medical records in a secure, private and proper manner. That is, it is important to ensure that medical records such as, for example, charts, x-rays, MRIs, sonograms, and other tests and procedures be maintained in a secure environment, e.g., such that only authorized persons are able to have access to such medical records. HIPAA also describes procedures to record the disclosure of medical information.

Although the medical industry, overall, has safeguards in place to securely maintain the records, other issues are also of concern. For example, consider the very busy medical staffs schedules and time pressures, manual processes and identification of the patients and other parties that would like access to a patient's medical records, such as friends or family members. This can lead to improperly handling of information by revealing information to parties that have not been properly authorized to view the information. HIPAA defines procedures for the inavertant disclosure of medical information to which close adherence is required.

SUMMARY

In a first aspect of the invention, a method implemented in a computer infrastructure having computer executable code tangibly embodied on a computer readable storage medium having programming instructions operable to: assign identification information to a plurality of users and a plurality of items; associate the identification information of a user of the plurality of users with one or more items of the plurality of items; set-up security policies including predetermined locations, within predetermined stages within a sequence and during predetermined times; and provide the user access to the one or more items when there is a matching between the identification information of the user and the one or more items, and all of the security policies associated with the user and the one or more of the plurality of items are met.

In another aspect of the invention, a system is implemented in hardware. The system comprises a computing infrastructure operable to set up security polices in order to provide access to medical information to one or more requesting users, in compliance with the security policies. The computing infrastructure is further operable to authorize or provide access to the medical information when all security policies are met including identification information of the one or more requesting users matches with identification of requested medical information, and the one or more requesting users and the requested medical information are at a set location, during a set time period at a defined event in a sequence of events.

In an additional aspect of the invention, a computer program product comprising a computer usable storage medium having readable program code embodied in the storage medium. The computer program product includes at least one component operable to: assign identification information to a plurality of users and a plurality of items; activate a radio frequency identification tag having the identification information; associate the activated radio frequency identification tag of at least one user of the plurality of users with one or more items of the plurality of items; set-up security policies to allow access to the one or more items of the plurality of items which include providing access only at predetermined locations, within a certain sequence and at predetermined times; provide the at least one user access to the one or more of the plurality of items when there is a match between the activated radio frequency identification tag of the at least one user and the identification information of the one or more of the plurality of items, and all of the security policies associated with the at least one user and the one or more of the plurality of items are met.

In a further aspect of the invention, a computer system provides secure access to medical information. The system comprises a CPU, a computer readable memory and a computer readable storage media. The system further comprises first program instructions to assign and manage radio frequency identification (RFID) information for one or more users and one or more items. The system further comprises second program instructions to manage the one or more items. The system further comprises third program instructions to set and maintain security policies comprising setting access permissions to the one or more items when the RFID information for one or more users match with the one or more items, and the matched one or more users and the one or more items are at predetermined locations, within predetermined stages within a sequence and during predetermined times in accordance with the security policies. The first, second and third program instructions are stored on the computer readable storage media for execution by the CPU via the computer readable memory.

In another aspect of the present invention, a method of deploying a system for securing medical information comprises providing a computer infrastructure, being operable to: assign identification information to a plurality of users and a plurality of items; set-up security policies including predetermined locations, within predetermined stages within a sequence and during predetermined times; and provide a user access to one or more of the plurality of items when there is a match between the identification information of the user and the one or more of the plurality of items, and all of the security policies associated with the user and the one or more of the plurality of items are met.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The present invention generally relates to managing of healthcare information in a secure manner and, more particularly, to a system and method for managing healthcare information (e.g., medical records). More specifically, the present invention provides a system and method for providing medical information to only authorized persons within or outside of a medical facility, e.g., hospital, outpatient surgery center, urgent care center, doctor's office, etc. based on certain predefined security policies (e.g., conditions or rules). The medical information can range from, for example, medical charts, tests, x-rays, CAT scans, MRI's, sonograms, etc., and can be in any media such as, for example, physical form (non-digital) or digital form displayed using electronic media tools such as web browsers, movie players, image viewers, etc.

In implementation, the system and method of the present invention can identify and record medical information throughout a medical facility, and provide access to the medical information to only authorized users, taking into consideration both temporal and location information. For example, in embodiments, the system and method of the present invention assigns all medical information and people unique identifiers via an RFID tag or other identification mechanism such as any type of biometrics, e.g., retina scan, fingerprints, etc. In embodiments using digital media, the medical information may be associated with a given identification, or a personal digital assistant (or other computing device) which displays the medical information may be given the unique identification. Using, for example, RFID readers, movement of the medical information and persons can be recorded and audited, periodically.

In any scenario, certain predefined security policies are associated with the medical information and people, using the unique identification information. The certain predefined security policies can be based on both temporal and defined location considerations. The certain predefined security policies may be provided by an administrator or a service provider such as, for example, a medical consulting firm. In any manner in which the predefined security policies are provided, the certain predefined security policies (hereinafter referred to generally as "security policies") may include, for example, designating certain people to have access to certain medical information at predetermined times and predetermined locations, e.g., only in an operating room, only in a pre-op room, only in a consultation room or combination thereof, etc. A person may access the medical information upon a match between the identification of the medical records and the security policies, e.g., an authorized person being in a certain location at a certain time. In this way, the given set of identifiers and security policies, e.g., a specified place and time, can be used to augment other security policies surrounding the medical information. This prevents unauthorized access to the medical information and greatly reduces the chances of showing the information to unauthorized parties.

System Environment

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
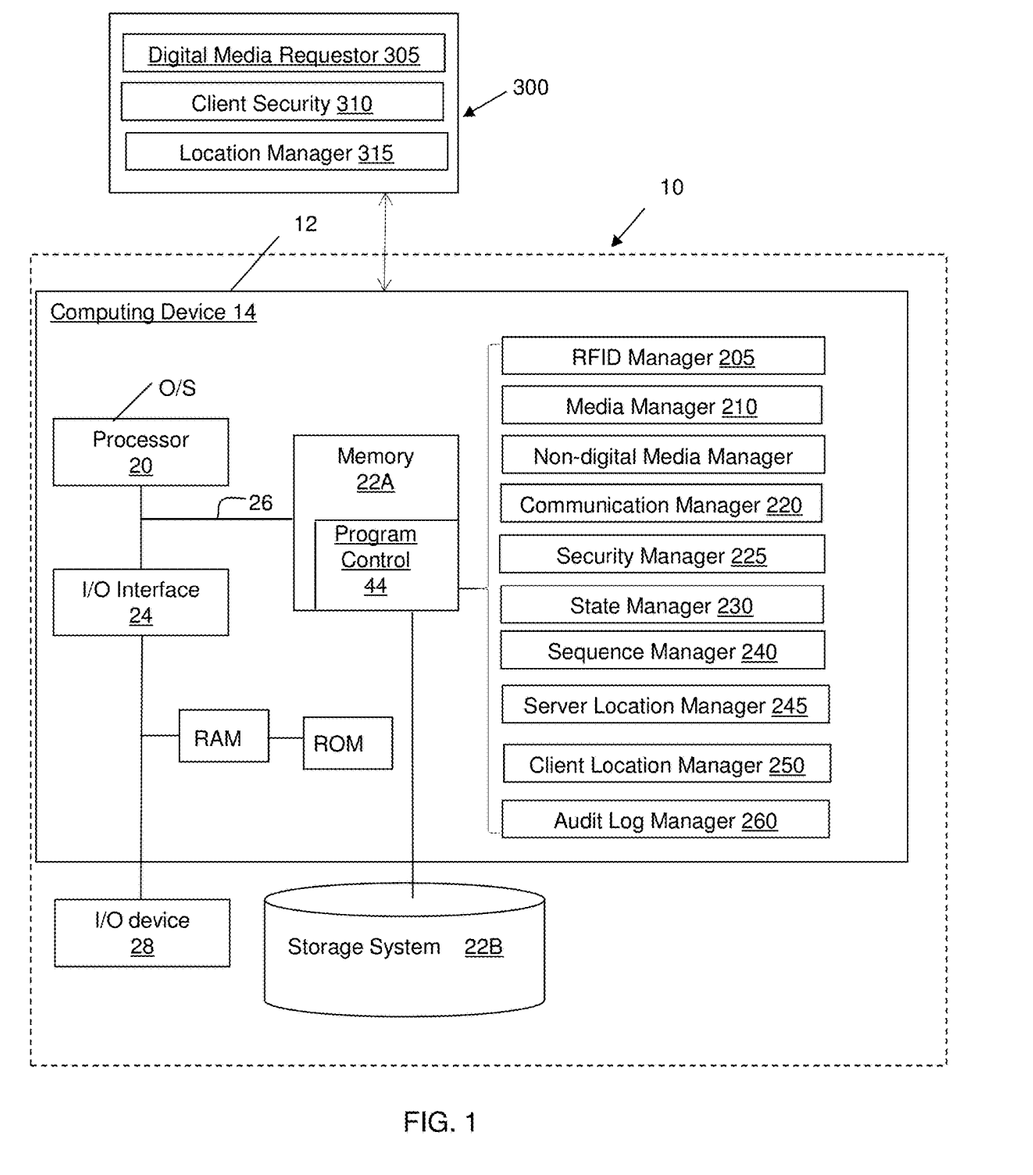
FIG. 1 an illustrative environment for implementing the steps in accordance with aspects of the invention.

FIG. 1 shows an illustrative environment 10 for managing the processes in accordance with the invention. To this extent, the environment 10 includes a server or other computing system 12 that can perform the processes described herein. In particular, the server 12 includes a computing device 14. The computing device 14 can be resident on a network infrastructure or computing device of a third party service provider (any of which is generally represented in FIG. 1).

The computing device 14 includes a processor 20, memory 22A, an I/O interface 24, and a bus 26. The memory 22A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 14 is in communication with the external I/O device/resource 28 and the storage system 22B. For example, the I/O device 28 can comprise any device that enables an individual to interact with the computing device 14 (e.g., user interface) or any device that enables the computing device 14 to communicate with one or more other computing devices using any type of communications link. The external I/O device/resource 28 may be for example, a handheld device, PDA, handset, keyboard etc. The computing device 14 is also in communication with a client 300 (user requesting medical information).

In general, the processor 20 executes computer program code (e.g., program control 44), which can be stored in the memory 22A and/or storage system 22B. Moreover, in accordance with aspects of the invention, the program control 44 controls several modules 205, 210, 215, 220, 225, 230, 240, 245, 250 and 260 which can perform the processes described herein. The modules 205, 210, 215, 220, 225, 230, 240, 245, 250 and 260 can be implemented as one or more program code in the program control 44 stored in memory 22A as separate or combined modules. Additionally, the modules 205, 210, 215, 220, 225, 230, 240, 245, 250 and 260 may be implemented as separate dedicated processors or a single or several processors to provide the function of these tools. The modules 205, 210, 215, 220, 225, 230, 240, 245, 250 and 260 may communicate with each other or other components described herein through any of the communications systems discussed herein, e.g., bus 26, wireless communications, etc. While executing the computer program code, the processor 20 can read and/or write data to/from memory 22A, storage system 22B, and/or I/O interface 24. The bus 26 provides a communications link between each of the components in the computing device 14.

In embodiments, each of the modules 205, 210, 215, 220, 225, 230, 240, 245, 250 and 260 has a specific set of responsibilities. In particular, an RFID Manager 205 is operable to assign an RFID tag to a given person or item, e.g., medical information. It should be understood by those of skill in the art that the present invention is not limited to an RFID configuration and, for example, can equally be implemented with other protocols known to those of skill in the art. As the present invention is not limited to RFID technology, it should further be understood by those of skill in the art that the RFID Manager, for example, can be a manager of other technologies contemplated herein. However, for sake of illustrative examples, RFID and related technologies are described herein, without imposing any limitations on the present invention.

The RFID Manager 205 is further operable to determine if a given RFID tag is active in the system. That is, the RFID Manager 205 can determine, for example, whether a given RFID tag has been activated and remains within a given facility or location. The RFID Manager 205 is further operable to determine and/or record the location of a given RFID tag, via RFID readers. This can be accomplished by reading RFID information as an RFID tag enters and/or exits certain rooms or other areas. The RFID Manager 205 is further operable to determine whether there is a duplicate detection of a given RFID tag (or other type of identification), in which case the RFID Manager 205 may disable all of the RFID tags associated with the particular duplicate identification so that unauthorized users cannot gain access to the medical information, for example. The RFID Manager 205, upon a breach of other security policies, may also disable RFID tags and/or deny access to certain medical information. In this way, upon a triggering or breach of a security policy, e.g., duplicate RFID tags, the system and method of the present invention will ensure that unauthorized access to medical records is not possible.

A Media Manager 210 is operable to manage all digital media. For example, the Media Manager 210 can manage, but not limited to:

Encrypting all digital media such as, for example, MRI, CAT scan and x-rays as they are created;

Checking with a Security Manager 225 if a given requester may access a given media item before delivering the encrypted media;

Recording all persons that requested media and what media was requested by sending a message to the Audit Log Manager 260 (e.g., historical data); and/or Destroying any digital media per security policies.

The Digital Media Manager 210 can send alerts to a Communication Manager 220 when a given digital media security policy has been violated, e.g., a film x-ray moved into a location, at a place and time that does not match what is defined in the security policy for that item. The Digital Media Manager 210 can also record movement of RFID tagged digital media, for example.

A Non-digital Media Manager 215 can manage any non-digital media such as film x-rays that have an RFID tag. The Non-digital Media Manager 215 can manage, but not limited to:
  Checking with a Security Manager 225 if a given requester may access a given non-digital media item before providing access to such non-digital media;
  Recording all persons that requested non-digital media and what non-digital media was requested by sending a message to the Audit Log Manager 260; and/or
  Requesting and/or instructing destruction of any non-digital media per security policies.

The Non-digital Media Manager 215 can also send alerts to the Communication Manager 220 when a given non-digital media security policy has been violated, e.g., a film x-ray moved into a location, at a place and time that does not match what is defined in the security policy for that item. The Non-digital Media Manager 215 can also record movement of RFID tagged non-digital media, for example.

The Communication Manager 220 handles all communication between the client 300 and the server and components thereof, including transport level encryption. For example, the Communication Manager 220 is operable to handle all intra-component communications, and can additionally send alerts to pagers, cell phones, Electronic Medical Records (EMR) or other communication devices, per a breach of a security policy, e.g., EMR configuration or preferences, etc.

The Security Manager 225 maintains the security policies which may be set up by a third party administrator. In embodiments, the security polices can define who is allowed to view certain medical information, at certain times and at certain locations. For example, the security policies may be, for example, standard policies set up by a service provider or other third party, off-site from the medical facility. In embodiments, for example, an administrator will configure or set up the security policies prior to a patient entering a medical facility and being assigned an RFID tag. The Security Manager 225 can, of course, allow the administrator to remove, alter or modify any security policy. In this way, as a third party administrator is responsible for setting up and maintaining the security policies, it is not possible for someone to tamper and/or change any security policy when assigning the RFID tag, thereby ensuring that the medical information will be correctly matched to the correct persons.

The Security Manager 225 can also provide, for example, authentication, authorization and access rights to all medical information registered with the system, and can implement a mutual authentication method such that the client is assured it is communicating with an authorized server and the server is assured it is communicating with an authorized client. For example, methods such as exchange of SSL (secure socket layer) certificates may be implemented with the present invention.

In further embodiments, the Security Manager 225 provides key structures for encryption and can compute and provide hash values for all data, e.g., medical information, RFID information, etc. By way of illustration, the hash can be used for data integrity, e.g., making sure what was sent was the same as what was received. The Security Manager 225 further coordinates with the Sequence Manager 240 to determine if access to a given item (e.g., medical information) should be provided in a given place at a given time, e.g., a medical professional should not be reviewing a non-family member's post-op media in a consolation room while the patient is in pre-op. This feature ensures that the medical information, for example, is being viewed at a proper time, thereby ensuring that the medical information is associated with the person in consultation or surgery, as examples.

The State Manager 230 is configured to coordinate with the RFID Manager 205 to set the state of a given RFID tag's location. For example, the tag id 1234 last location was the waiting area, was read on the waiting room reader and then read on the family consolation area reader. Therefore, in this example, the State Manager 230 determines that the state of tag id 1234 is in the family consolation area.

The Sequence Manager 240 controls what types of medical information may be presented at a certain location and/or time based on a sequence of events. Accordingly, the occurrence of an event in a certain sequence may be a security policy, which will ensure that medical information can be shown (provided and/or exchanged) at certain locations and times to certain authorized users based on an event occurring within a certain sequence. In this way, medical information can be shared amongst certain identified and authorized persons at only certain times and in certain locations thereby ensuring that medical information is not shared with unauthorized persons at unauthorized times and locations.

The Sequence Manager 240 may set any number of sequences as a security policy. The Sequence Manager 240 can also allow the administrator to modify any current sequence, remove any given sequence and/or add a sequence. For example, a security policy based on a sequence of events may include, but not limited to:
  X-rays of post operative results can be shown to a patient only after a surgery and in a post operative recovery area;
  X-rays of post operative results cannot be shown to a patient in pre-operative testing (since the patient did not have surgery); and/or
  Pre operative blood tests can be provided in a preoperative setting and a surgical suite at a time of a surgery.

Illustratively, it is possible for a patient to return to pre-op from surgery due to unforeseen issues. Based on the sequence of events set by the Sequence Manager 240, it will not be possible for a doctor to show a family post-op x-rays because the Sequence Manager 240 required the patient's RFID tag to move into post-op, which would indicate that the person should not shown post operative x-rays. The sequence may be provided to the Security Manager 225 for enforcement, for example.

Also, it should be understood by those of skill in the art that each step in the sequence may include one or more states. For example, the following table provides some examples of security policies, with different states. The table includes, for example, an identification that has been provided to the patient, medical information, RFIDs associated with, e.g., family members, medical professional and others that may be authorized to have access to the medical information, as well as start and end dates and a sequence. These security policies may be stored in the storage system 22B.

| Patient ID | Media ID | Location(s) (state) | RFID(s) | Start date | End date | Sequence |
|---|---|---|---|---|---|---|
| 123 | 456<br>234<br>567 | Doctor-family consultation area<br>Pre Op. area | 900<br>789<br>790<br>791 | Jan. 2, 2010 10:00 AM | Jan. 3, 2010 10:00 AM | Outpatient surgery |
| 123 | 345<br>456 | Post Op. Recovery Area | 900<br>789<br>790 | Jan. 2, 2010 11:00 AM | Jan. 3, 2010 11:00 AM | Outpatient surgery |
| 123 | (any) | Doctor's consolation area | 900<br>901<br>902<br>903<br>904 | Jan. 2, 2010 1:00 AM | Jan. 2, 2011 1:00 AM | Outpatient surgery<br>Testing |
| 125 | 457 | Stress test lab | 900<br>901 | (any) | (any) | Testing |

By way of explanation of the above table, in all cases, the Patient's ID, also an RFID, is automatically included in the RFID column, as a patient is always entitled to see their own medical information. In the above table, by way of further explanation, RFIDs 900, 789, 790 and 791 can have access to medical information with ID 456, 234 and 567 from Jan. 2, 2010 at 10:00 AM to 10:00 AM on Jan. 3, 2010, at the family consultation area and pre-operative area during an out-patient surgical procedure.

A Server Location Manager 245 is operable to provide location information of a given person or item. For example, the Server Location Manager 245 can determine whether a patient is in the pre-op room or an x-ray film is in the family consolation room. This can be accomplished by interacting with the State Manager 230 to provide such location information. This location information can be obtained by an RFID reader or other location mechanism such as, for example, GPS or triangulation methods using active RF frequencies.

The Client Location Manager 250 is operable to assign a given RFID tag to a person or item such as, for example, medical information. This can be accomplished by, for example, sending a message to the system that the person or medical information is now at a specific RFID reader. No manual keying of the serial number is required or supported as human data entry can be error prone. Also, the Client Location Manager 250 can remove a given RFID tag from the system by sending a message to the system requesting to deactivate a given RFID.

The Audit Log Manager 260 is responsible for storing and retrieving medical information disclosures. For example, the Audit Log Manager 260 stores a given disclosure into and retrieves requested disclosures' by interacting with storage system 22B. The Audit Log Manager 260 receives messages from the Media Manager 210. An example of the structure of this message may be seen in FIG. 5.

The computing device 14 can comprise any general purpose computing article of manufacture capable of executing computer program code installed thereon (e.g., a personal computer, server, etc.). However, it is understood that the computing device 14 is only representative of various possible equivalent-computing devices that may perform the processes described herein. To this extent, in embodiments, the functionality provided by the computing device 14 can be implemented by a computing article of manufacture that includes any combination of general and/or specific purpose hardware and/or computer program code. In each embodiment, the program code and hardware can be created using standard programming and engineering techniques, respectively.

Similarly, the server 12 is only illustrative of various types of computer infrastructures for implementing the invention. For example, in embodiments, the server 12 comprises two or more computing devices (e.g., a server cluster) that communicate over any type of communications link, such as a network, a shared memory, or the like, to perform the process described herein. Further, while performing the processes described herein, one or more computing devices on the server 12 can communicate with one or more other computing devices external to the server 12 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

The server 12 and/or computing device 14 can communicate with a client, e.g., medical professional, 300 by the communications link which can comprise any combination of wired and/or wireless links; any combination of one or more types of networks (e.g., the Internet, a wide area network, a local area network, a virtual private network, etc.); and/or utilize any combination of transmission techniques and protocols. The client 300 includes a Digital Media Requester 305, which can request certain medical information for a given patient. In embodiments, the Digital Media Requester 305 communicates with the Client Security Module 310, which provides keys and other data required for authentication or access to the system 12. The client 300 also includes a Location Manager 315, which can provide location information for the client.

The Client Security Module 310 can perform many functions such as, for example, Stores all keys and other data required for authentication such as SSL certificates;

Implements a mutual authentication method such that the client is assured it is communicating with an authorized server and the server is assured it is communicating with an authorized client. Methods such as exchange of SSL certificates may be used;

Provides decryption methods (e.g., no digital information may be decrypted unless at least one security policy has been meet);

Communicates with the Security Manager 225 to negotiate security protocols;

Computes the hash value of all data received and compares it to the hash computed by the Security Manager 225. This ensures data integrity by comparing the data sent to what was received; and/or Authenticates the user.

In further embodiments, the Client Security Module 310 can provide a security feedback loop that uses the patents' picture to confirm the RFID tag was assigned to the correct person. That is, the Client Security Module 310 can display a patent's picture for, e.g., a family member, to confirm they are with the correct person.

In embodiments, the security model used by the present invention thus reduces the possibility of a "man in the middle" or information being overheard. This is because, for example, all data is stored and transmitted using an encryption that is separate from the transport, which is also encrypted. As another example, both the client 300 and server 12 mutually authenticate to the other, and both location and temporal data is used in the security policies. In addition, users authenticate to the client 300, and the data hashes are used to ensure data integrity.

Illustrative Environment and Example of Use

As described herein, the present invention implements RFID tags to enhance security policies surrounding access to medical information; although other mechanisms and information are also contemplated by the present invention. In the present invention, the RFID tags are used as a publicly readable name tag that informs the system as to the current and historic location of any given tag. The security policies use this information to augment security policies and measures, as described above, such that a given piece of medical information is only viewable at a given time and place when the correct RFID tags are present and the requester has been authenticated and authorized per the systems security policies. In this way, even if a given RFID tag has been cloned or lost and used by someone other than the original assigned person, the system will not allow medical information to be presented without the remainder of the security policies being met. Accordingly, in implementation, it becomes possible for the system to identify a misused or cloned RFID because, for example, (i) the ID will show in the wrong place at the wrong time, (ii) the same ID will show up in two different locations at the same time, or (iii) an impossible route or distance apart between reads has been detected. Should such condition be detected, the system can respond by locking all medical information the ID has been authorized to view until an administrator clears the lock.

Figure 2:
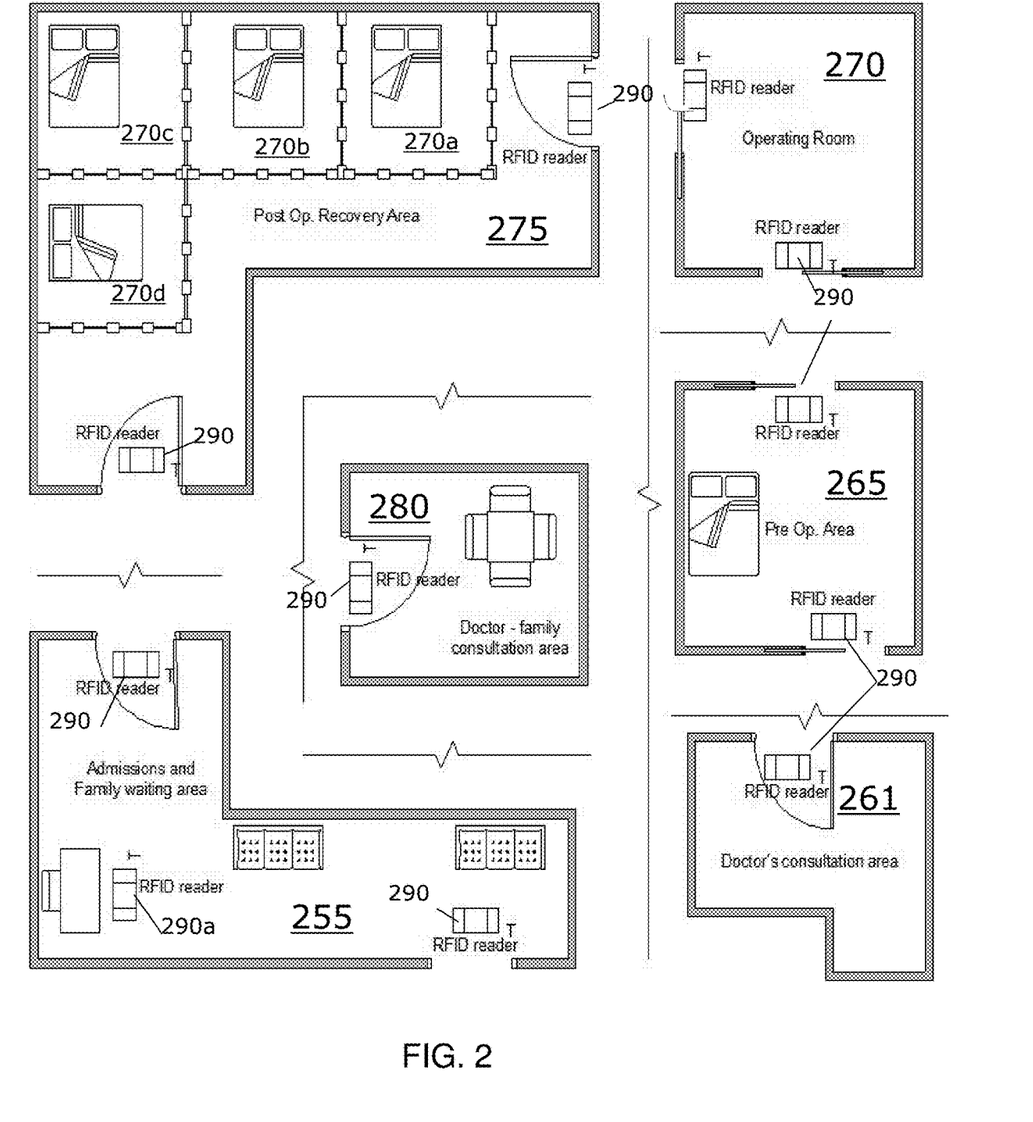
FIG. 2 shows an illustrative environmental implementation of the invention.

FIG. 2 shows a typical hospital out-patient surgery scenario implementing the aspects of the present invention. However, it should be understood by those of skill in the art that the present invention is not limited to a out-patient surgery scenario, and can equally be implemented in other settings such as, for example, a doctor's office, an inpatient care facility, etc.

More specifically, FIG. 2 shows several zones, e.g., areas, for a typical hospital surgery facility. These areas include, for example, a reception or admission area 255, a consultation room 261, pre-operative area 265, operating room 270, post recovery area 275 (with discrete areas 275a, 275b, 275c, 275d, etc.) and family consultation room 280. All entrances and exits have RFID readers 290, with an additional RFID reader 290a at the admissions desk of the reception area 255. The RFID readers 290 can identify all persons and medical information throughout the facility, e.g., hospital out-patient surgery. This allows the system of the present invention, e.g., modules 205, 210, 215, 220, 225, 230, 240, 245, 250 and 260, to manage the processes of the present invention, e.g., access to medical information at certain times, at certain locations, within a certain sequence of events, to certain authorized persons.

At the reception area 255, the patient and other soon to be authorized persons, e.g., family members, are provided with RFID tag(s). The RFID tags can be in the form of a bracelet or key ring fob that is easily removed, and preferably does not require any personal information to be encoded or available on the RFID tags. Once an RFID tag is provided to a person(s), the person(s) will activate the tag, via the RFID Manager 205, by allowing the RFID tag to be read by the RFID reader 290a. This process will assign the RFID tag to a certain person(s). In this way, the act of assigning a given RFID tag to a given person is an active event and prevents mis-assignment of tags. Once the RFID tag is activated, the security polices will be associated with the RFID tag information. This can be done through a look up table stored in the storage system 22B of FIG. 1.

As the RFID tag moves across or by any given reader 290, the system records the change in location state for the person or medical information that was assigned to the RFID tag. For example, tag ID 1234, assigned to John Smith, has moved into the post operative recovery area 275, can be recorded by the RFID Manager 205. As another example, non-digital media such as x-ray film, medical charts, etc. assigned to ID 235 moved into the post operative recover area 275, can be properly recorded, monitored and/or recorded. Any movement of the medical information and/or person(s) can be read by the RFID readers 290 and provided to the modules of FIG. 1 for managing of such media and implementing the security policies to allow access to the media, e.g., medical information, by authorized persons.

The security policies, maintained in the Security Manager 225, define what information may be viewed by which authorized persons at which times and at what locations, e.g., 255-275, etc. For example, the security policies may be based on the combination of the unique identifiers, time and place, and may include locations where authorized persons need to view information in a special context and when as determined by either a combination of state or sequence such as, e.g., no post operation (sequence) x-rays (media), may be viewed until the patient is in the recovery room (state).

Authentication, authorization and access are handled by the Security Manager 225, described above. For example, the Security Manager 225 maintains the security policies which may be set up by a third party administrator; whereas, encryption and decryption of digital medical information may be performed by the Media Manager 210, and accessed by the client 300 shown in FIG. 1, based on such security policies. In embodiments, the system optionally sends an alert via beeper, hand held device or a laptop (e.g., client 300) warning a party, e.g., service provider, medical personnel, etc., that the unique ID of the person and medical information do not match the security policies for the area, sequence and/or time.

Flow Diagram

Figure 3:
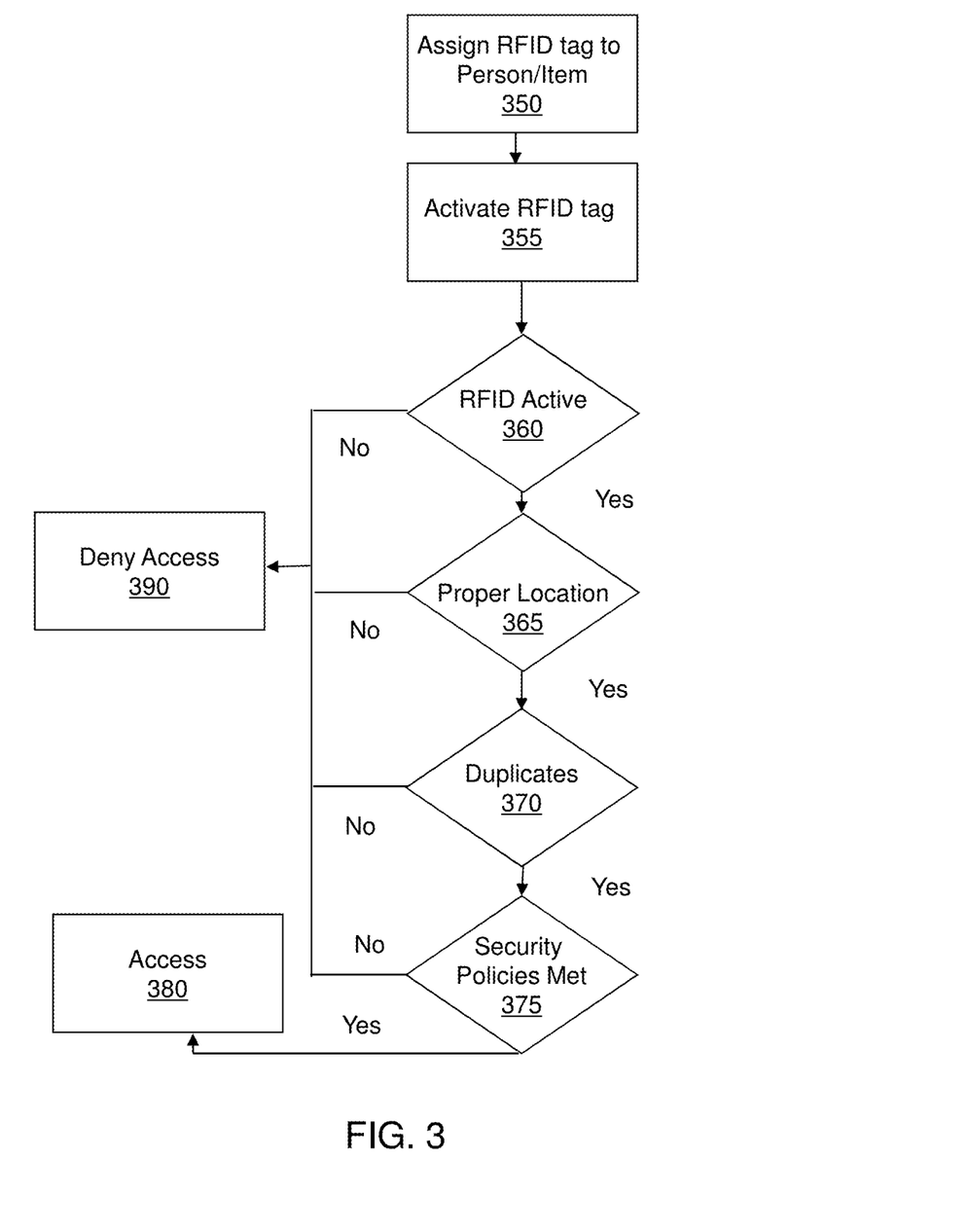
FIGS. 3 and 4 show exemplary flows in accordance with aspects of the invention.
Figure 4:
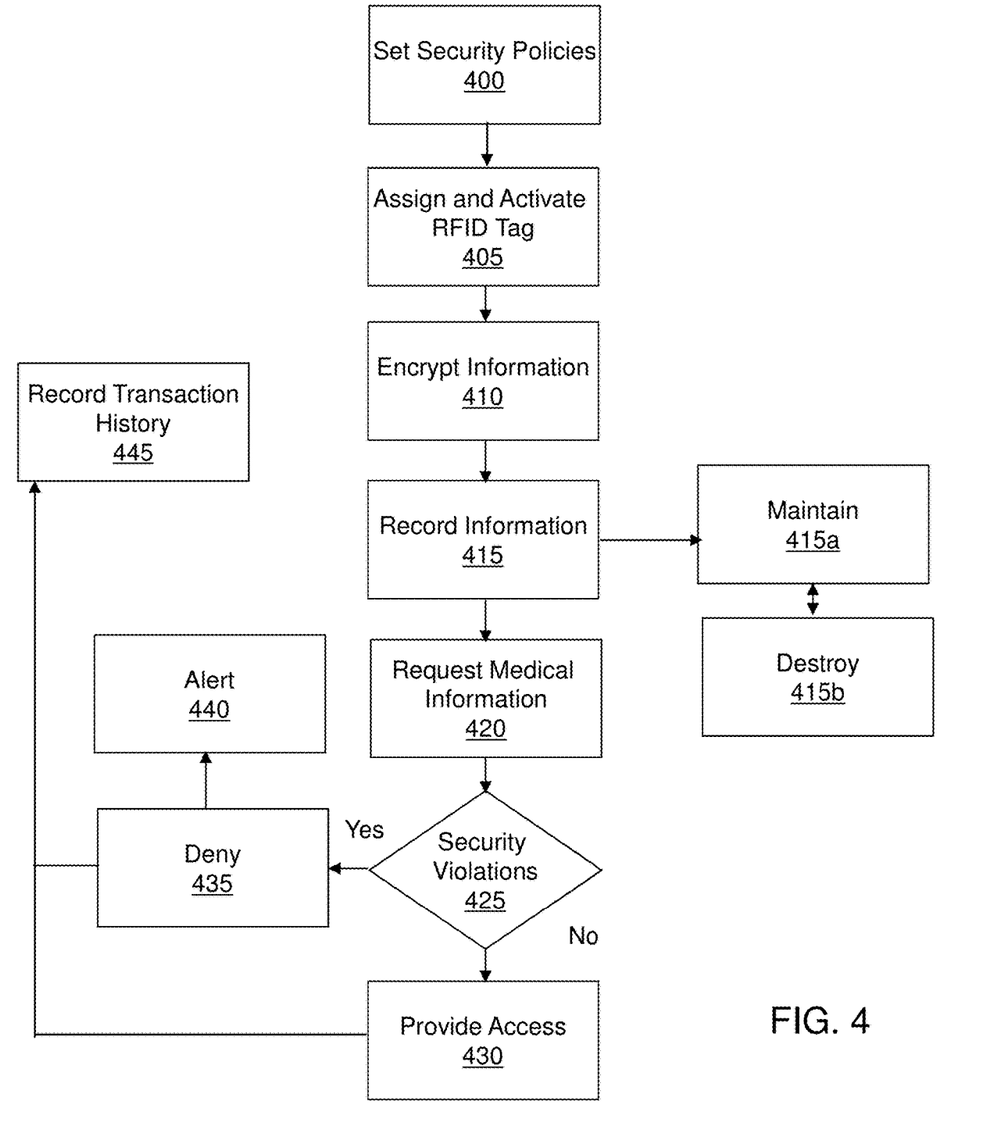

FIGS. 3 and 4 show exemplary flows for performing aspects of the present invention. The steps of FIGS. 3 and 4 may be implemented in the environment of FIG. 1, for example. The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Furthermore, the invention can take the form of a computer program product accessible from a computer-usable or computer-readable medium providing program code for use by or in connection with a computer or any instruction execution system. The software and/or computer program product can be implemented in the environment of FIG. 1. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disc-read/write (CD-R/W) and DVD.

FIG. 3 depicts an exemplary flow for a process in accordance with aspects of the present invention. More specifically, FIG. 3 shows management of medical information in accordance with aspects of the present invention. At step 350, a person and medical information are assigned identification information, e.g., RFID tag. At step 355, the program control activates the RFID tag of the person(s). This may be accomplished by actively passing the RFID tag by an administrative RFID reader, for example. At step 360, the program control determines whether the RFID tag is active. If yes, the program control, at step 365, determines whether the RFID tag for the person and/or medical information are at a designated location, meeting the required security policies. This can be accomplished by use of RFID readers throughout a facility.

If yes, at step 370, the program control determines whether that there are duplicate or incorrect RFID tags. This can be accomplished, for example, by using a look up table in the storage system 22B. If there are no duplicates, mistakes, etc., at step 375, the program control determines whether all security policies have been met, e.g., place, time, sequence and state and matching between the user and medical information via, e.g., matching IDs. If all security policies have been met, at step 380, access to the medical information is provided by the client (in the case of digital media) or to any authorized persons. However, if any of the steps 360, 365, 370 and 375 are negative, access will be denied at step 390.

FIG. 4 shows additional processes in accordance with aspects of the present invention. It is again noteworthy to mention that the following sequence of processing steps do not have to be in the order noted herein. That is, two blocks shown in succession may, in fact, be executed substantially concurrently, or the blocks may sometimes be executed in the reverse order, depending upon the functionality involved. For example, recording of transaction history may be performed at any time within the process.

At step 400, an administrator sets security policies for access and/or management of medical information. At step 405, the RFID tag is assigned, typically by medical staff personnel, and activated by the present system. At step 410, information such as, for example, medical information, RFID information, etc. is encrypted for security purposes. At step 415, medical information can be recorded and/or any other encrypted information can be recorded, e.g., stored. At steps 415a and 415b, a decision can be made to maintain or destroy the recorded information, depending on predetermined policies. For example, medical information may be destroyed after a certain amount of time has elapsed, e.g., "X" number of years, or RFID information can be destroyed when the person is discharged from the medical facility.

At step 420, a client will request medical information. At step 425, the program control will determine whether all security policies have been met. If so, at step 430, the program control will provide access to the medical information. Access can be provided after authentication and authorization protocols have been established and met. The access can also include, for example, the decryption of the medical information, at the client side. If there are any security breaches, at step 435, the program control will deny access and provide an alert at step 440. At step 445, all transactions can be recorded. These transactions can include, for example, who obtained specific medical information at certain locations, times and within what sequence of events.

In embodiments, a service provider, such as a Solution Integrator, could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

Figure 5:
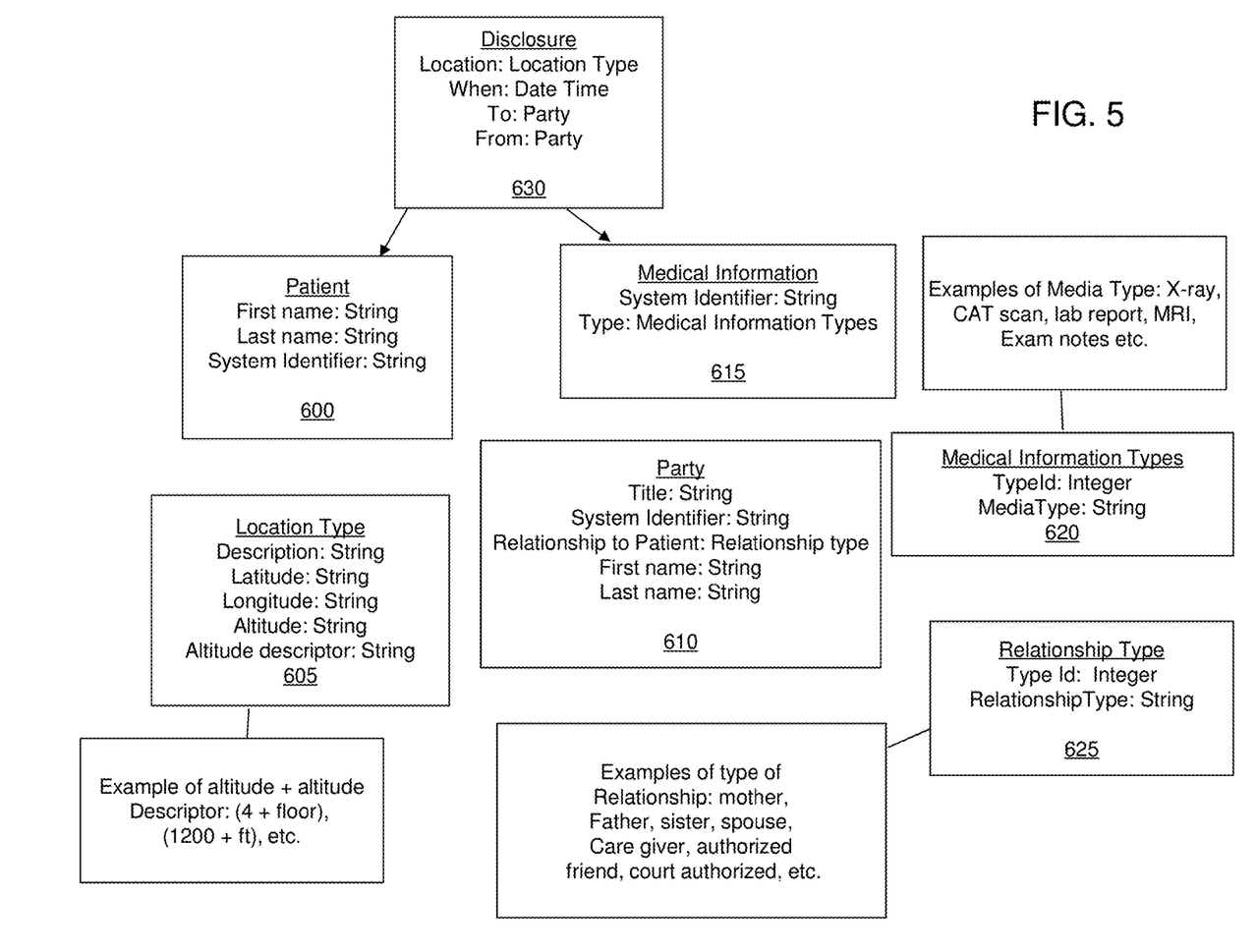
FIG. 5 shows the data structure used by the Audit log manager component in accordance with aspects of the invention.

FIG. 5 shows the data structure used by the Audit Log Manager component 260 in accordance with aspects of the invention. The components can record information such as, for example, patient information 600, location information 605 (e.g., $4^{th}$ floor), party information 610, medical information 615, medical information type 620 (e.g., CAT scan), and relationship information 625 (e.g., family relations). The components can also include disclosure information 630. The disclosure information may include administrative information such as, from, by, location and time entries.

Accordingly, the present invention provides a mechanism to control access to medical information via secure methods by logging all disclosures using unique identifiers that are physically assigned to people and things via RFID tags. A security model is defined that requires authentication, and includes a location and temporal data to access specific medical information. Technologies such as Radio Frequency Identification (RFID), Public/Private key encryption and SSL layers are employed to secure medical information allowing the medical personnel to disclose the information only to the correct people at the correct time without the need for deliberately scanning or other manual process.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims, if applicable, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principals of the invention and the practical application, and to enable others of ordinary skill in the art to understand the invention for various embodiments with various modifications as are suited to the particular use contemplated. Accordingly, while the invention has been described in terms of embodiments, those of skill in the art will recognize that the invention can be practiced with modifications and in the spirit and scope of the appended claims.

What is claimed is:

1. A computer system for providing secure access to medical information, the system comprising:
    a CPU, a computer readable memory, and a computer readable storage media;
    program instructions to activate one or more RFID tags;
    program instructions to record one or more locations of the one or more RFID tags when each of the one or more RFID tags enters and exits a respective location of the one or more locations;
    program instructions to determine whether one or more items include medical information and RFID information;
    program instructions to encrypt and store the medical information and RFID information in response to determining that the one or more items include medical information and RFID information;
    program instructions to destroy the encrypted and stored medical information and RFID information after a predetermined time period has elapsed;
    program instructions to provide a user access to the one or more items when there is a matching between an RFID tag of the user and one or more RFID tags associated with the one or more items, and all security policies associated with the user and the one or more items are met, wherein:
        the security polices include a predetermined authorized location, a predetermined authorized time, and a predetermined authorized stage within a sequence of events for authorized persons to view information from the one or more items in a context as determined by a combination of the predetermined authorized location and the sequence of events, and the matching comprises determining that the RFID tag of the user and the one or more RFID tags of the one or more items are recorded at the predetermined authorized location at the predetermined authorized time, within the predetermined authorized stage within the sequence of events, and
    program instructions to lock the one or more items in response to the one or more RFID tags associated with the one or more items showing up in two different locations at a same time;
    program instructions to determine whether the RFID tag of the user is a duplicate RFID tag;
    program instructions to disable the RFID tag of the user in response to determining that the RFID tag of the user is the duplicate RFID tag; and
    program instructions to record a plurality of transactions associated with the user access being provided to the one or more items, the transactions including a person who obtained medical information at a location, a time associated with the obtained medical information at the location, and the sequence of events associated with the obtained medical information at the location,
        wherein the program instructions to provide the user access to the one or more items further comprises decrypting the encrypted and stored medical information and RFID information, and
        wherein the program instructions are stored on the computer readable storage media for execution by the CPU via the computer readable memory.

2. The computer system of claim 1, wherein the encrypted digital and stored medical information comprises digital medical information which is associated with a predetermined identification and is configured to be displayed by a web browser and an image viewer on a computing device of the user using the predetermined identification.

3. The computer system of claim 2, wherein a client side system is authenticated prior to the providing the user access of the encrypted digital medical information, and the client side system decrypts the encrypted and stored medical information, denies access to the user in response to a security breach, and sends an alert to a handheld device that the security breach has occurred.

4. The computer system of claim 1, further comprising program instructions to determine that the RFID tag of the user is not the duplicate RFID tag or incorrect prior to providing the user access by using a lookup table in a storage system.

5. The computer system of claim 4, further comprising:
    program instructions to send alerts to Electronic Medical Records (EMRs) when the RFID tag of the user is the duplicate RFID tag or incorrect;
    program instructions to manage the one or more items, including:
    encrypting all digital media comprising MRI, CAT scan, and X-rays representative of the one or more items;
    recording all users that requested any of the one or more items and what items of the one or more items was requested by sending a message to a log manager;
    destroying any of the one or more items per security policies after the predetermined period has elapsed; and
    sending alerts to a plurality of cell phones when the security policies have been violated,
    wherein the program instructions are stored on the computer readable storage medium for execution by the CPU via the computer readable memory.

6. The computer system of claim 1, further comprising program instructions to determine that the one or more RFID tags are active and are in a designated location prior to the providing the user access to the one or more items by using RFID readers throughout a facility.

7. The computer system of claim 1, further comprising program instructions to record a location of the RFID tag of the user and the one or more items or a system that displays digital media of the one or more items using a personal digital assistant with a predetermined identification.

8. The computer system of claim 1, wherein the one or more items comprise portable RFID tagged digital media which can be recorded using a digital media manager.

9. The computer system of claim 1, further comprising program instructions to provide authentication and authorization rights using secure socket layer (SSL) certificates to all registered medical information that meet the security policies.

10. The computer system of claim 1, wherein the one or more items comprise non-digital media comprising X-ray film and medical charts which are recorded and monitored.

11. The computer system of claim 1, further comprising a client security module adapted to utilize a user's picture to confirm the RFID tag of a user was assigned to a correct user and display the user's picture to a family member to confirm that the user is the correct user.

12. The computer system of claim 1, further comprising providing a security feedback loop by implementing a client security module adapted to display a user's picture to a second user to confirm the RFID tag of a user was assigned correctly to the user, wherein the providing access to the one or more items when the security policies are met includes matching identification information of the user in the security policies with identification information of the one or more items in the security policies, the client security module stores all keys required for authentication of the RFID tag of the user such as SSL certificates, the client security module implements a mutual authentication of the information of the one or more items by assuring an authorized server and the server is communicating with an authorized client and the authorized server is assured it is communicating with the authorized client, the client security module provides decryption for digital information of the one or more items, the client security module communicates with a security manager to negotiate security protocols of the security policies, the client security module computes a hash value of all data received and compares it to hash values computed by the security manager to verify an integrity of the one or more items by comparing the data which was sent to what was received, and the security policies are setup prior to the user entering a medical facility and being assigned the RFID tag.

13. A computer program product comprising a computer usable storage device having readable program code embodied in the storage device, the computer program product includes at least one component operable to:
  activate one or more RFID tags;
  record one or more locations of the one or more RFID tags when each of the one or more RFID tags enters and exits a respective location of the one or more locations;
  determine whether the one or more RFID tags is a duplicate by using a look up table in the storage device;
  verify an integrity of one or more items by comparing hash values associated with the one or more items to hash values computed for the one or more items;
  determine whether the one or more items include medical information and RFID information;
  encrypt and store the medical information and RFID information in response to determining that the one or more items include medical information and RFID information;
  destroy the encrypted and stored medical information and RFID information after a predetermined time period has elapsed;
  provide a user access to the verified the one or more items when the one or more RFID tags has no duplicate and there is a match between an RFID tag of a user and one or more RFID tags of the one or more items, and all of the security policies associated with the user and the one or more items are met; and
  lock the one or more items in response to a determination that the one or more RFID tags is duplicated;
  determine whether the RFID tag of the user is a duplicate RFID tag;
  disable the RFID tag of the user in response to determining that the RFID tag of the user is the duplicate RFID tag; and
  record a plurality of transactions associated with the user access being provided to the one or more items, the transactions including a person who obtained medical information at a location, a time associated with the obtained medical information at the location, and the sequence of events associated with the obtained medical information at the location,
  wherein the match comprises determining that the RFID tag of the user and the one or more RFID tags of the one or more items are recorded at a predetermined location at a predetermined time within a predetermined stage within a sequence of events and a state of different predetermined locations at predetermined times included in the security policies for authorized persons to view information from the one or more items in a context as determined by a combination of the predetermined stage within the sequence of events and the state of different predetermined locations at the predetermined times,
  the providing the user access to the one or more items includes decryption of the encrypted and stored medical information and RFID information, and
  the encrypted and stored medical information includes medical charts, tests, x-rays, CAT scans, MRIs, and sonograms.

14. The computer program product of claim 13, wherein the one or more items comprise nondigital or digital media, and the computer program product includes at least one component operable to:
  manage the one or more items, including:
    encrypting all digital media comprising the MRIs, the CAT scans, the tests, the x-rays, and the sonograms representative of the one or more items;
    checking with a Security Manager if the user may access the one or more items;
    recording all users that requested any of the one or more items and what items of the one or more items was requested by sending a message to a log manager;
    destroying any of the one or more items per security policies after the predetermined period has elapsed;
    sending alerts to a plurality of cell phones when the security policies have been violated;
    locking all the information from the one or more items in response to the one or more RFID tags showing in a wrong place at a wrong time, the one or more RFID tags showing up in two different locations at a same time, or an impossible route or distance apart between reads of the one or more RFID tags has been detected; and decrypting the encrypted digital media when the security policies have been met.

15. The computer program product of claim 14, wherein the providing the user access to the verified one or more items when all of the securities policies associated with the user and the one or more items are met includes matching identification information of the user in the security policies with identification information of the one or more items in the security policies.

16. The computer program product of claim 15, further comprising a client security module adapted to utilize a user's picture to confirm the RFID tag of a user was assigned to a correct user and display the user's picture to a family member to confirm that the user is the correct user.

17. The computer program product of claim 16, wherein the is encrypted digital and stored medical information comprises digital medical information which is associated with a predetermined identification and is configured to be displayed by a web browser and an image viewer on a computing device of the user using the predetermined identification.

18. The computer program product of claim 17, wherein a client side system is authenticated prior to the providing the user access of the encrypted and stored medical information, and the client side system decrypts the encrypted and stored medical information, denies access to the user in response to a security breach, and sends an alert to a handheld device that the security breach has occurred, the security policies are associated with the RFID tag of a user by using the look up table stored in the storage system, and the look up table includes columns for a patient ID, a media ID, state of different predetermined locations, RFID tag numbers, a start date, an end date and the sequence of events.

19. The computer program product of claim 13, wherein the at least one component is further operable to:

determine that the RFID tag of the user is the duplicate RFID tag or incorrect prior to providing the user access by using a lookup table in a storage system; and send alerts to a plurality of cell phones indicating that the RFID tag of the user is the duplicate RFID tag or incorrect.

20. The computer program product of claim 13, wherein the one or more items comprise portable RFID-tagged digital media comprising X-ray film and medical charts which are recorded and monitored.

* * * * *